US010393665B2

(12) United States Patent
Ahuja et al.

(10) Patent No.: US 10,393,665 B2
(45) Date of Patent: Aug. 27, 2019

(54) SYSTEMS AND METHODS FOR DETECTING AN OPTICAL CHANGE INDICATING THE PRESENCE OF AN ANALYTE

(71) Applicant: Case Western Reserve University, Cleveland, OH (US)

(72) Inventors: Punkaj Ahuja, Cleveland, OH (US); Maria A. Peshkova, Cleveland, OH (US); Brian D. Hemphill, Cleveland, OH (US); Miklós Gratzl, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 114 days.

(21) Appl. No.: 15/313,369

(22) PCT Filed: May 22, 2015

(86) PCT No.: PCT/US2015/032102
§ 371 (c)(1),
(2) Date: Nov. 22, 2016

(87) PCT Pub. No.: WO2015/179725
PCT Pub. Date: Nov. 26, 2015

(65) Prior Publication Data
US 2017/0191942 A1 Jul. 6, 2017

Related U.S. Application Data

(60) Provisional application No. 62/001,661, filed on May 22, 2014.

(51) Int. Cl.
G01N 21/77 (2006.01)
G01N 21/80 (2006.01)
(Continued)

(52) U.S. Cl.
CPC .......... *G01N 21/78* (2013.01); *A61B 5/1486* (2013.01); *G01N 21/80* (2013.01); *G01N 33/492* (2013.01);
(Continued)

(58) Field of Classification Search
None
See application file for complete search history.

(56) References Cited

U.S. PATENT DOCUMENTS 5,081,041 A  1/1992 Yafuso et al.
5,098,659 A * 3/1992 Yim ................... A61B 5/14539
                                                422/82.06
2012/0183452 A1  7/2012 Schalkhammer

FOREIGN PATENT DOCUMENTS

WO  2012/021239 A2  2/2012

OTHER PUBLICATIONS

Punkaj Ahuja et al.; Disposable optical slide provides a snapshot of metabolic parameters from a drop of blood at the bedside; 2013 IEEE Point-of-Care Healthcare Technologies (PHT); Bangalore, India; Jan. 16-18, 2013; pp. 310-313.

(Continued)

Primary Examiner — Neil N Turk
(74) Attorney, Agent, or Firm — Tarolli, Sundheim, Covell & Tummino LLP

(57) ABSTRACT

One aspect of the present disclosure relates to an analyte sensor device. The analyte sensor device can include an optode layer that undergoes an optical change in the presence of an analyte. The analyte sensor device can also include a selectively-permeable membrane encapsulating the optode layer to form a stable membrane that that minimizes fouling of the analyte sensor device. The analyte sensor device can also include a plurality of microparticles
(Continued)

that suppress a background physical interference on a detection of the optical change of the optode layer.

13 Claims, 8 Drawing Sheets

(51) Int. Cl.
  *G01N 33/49*  (2006.01)
  *G01N 33/84*  (2006.01)
  *A61B 5/1486*  (2006.01)
  *G01N 21/78*  (2006.01)
  *C12Q 1/54*  (2006.01)

(52) U.S. Cl.
  CPC ......... *G01N 33/4925* (2013.01); *G01N 33/84* (2013.01); *C12Q 1/54* (2013.01); *G01N 2021/775* (2013.01); *G01N 2201/064* (2013.01)

(56) References Cited

OTHER PUBLICATIONS

Punkaj Ahuja et al.; Minimizing color interference from biological samples in optode-based measurements; Sensor and Actuators B: Chemical; 204 (2014); pp. 319-325.
Allen Moradian et al.; Continuous optical monitoring of aqueous amines in transflectance mode; Sensors and Actuators B: Chemical; 62 (2000); pp. 154-161.
International Search Report and Written Opinion for corresponding PCT Application No. PCT/US2015/032102; dated Sep. 22, 2015.

\* cited by examiner

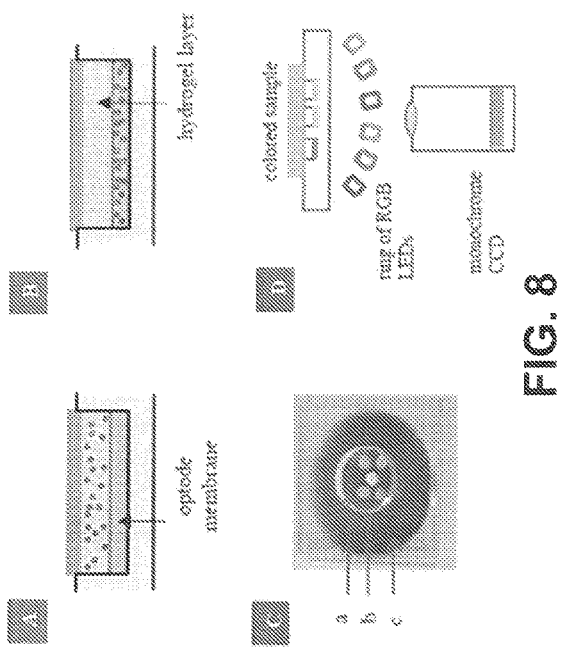
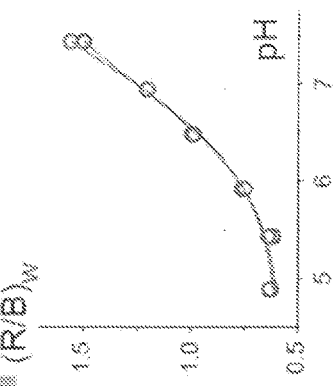
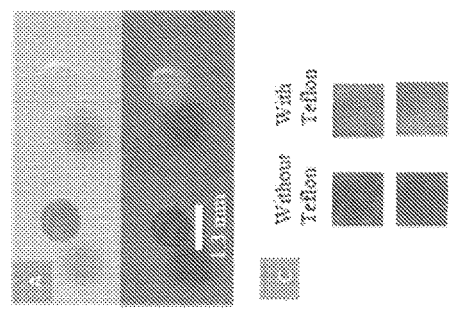
FIG. 8
FIG. 9

SYSTEMS AND METHODS FOR DETECTING AN OPTICAL CHANGE INDICATING THE PRESENCE OF AN ANALYTE

RELATED APPLICATION

This application is a U.S. National Stage Application under 35 USC 371, claiming priority to PCT Serial No. PCT/US2015/032102, filed on May 22, 2015; which claims priority to U.S. Provisional Patent Application No. 62/001,661, filed May 22, 2014, the entirety of both of which are incorporated herein by reference.

TECHNICAL FIELD

The present disclosure relates generally to systems and methods for detecting an optical change indicating the presence of an analyte and, more specifically, to systems and methods that can suppress a background physical interference during detection of the optical change.

BACKGROUND

Optodes are chemical sensors that respond to the presence of an analyte (e.g., oxygen, protons (pH), sodium, potassium, glucose, or the like) with a detectable change in an optical characteristic. With the development of improved imaging techniques, optodes now provide a viable alternative to electrode-based sensors and more complicated analytical instrumentation. However, even as imaging techniques improve, the detection of the change in the optical characteristic can be marred by background physical interferences.

SUMMARY

The present disclosure relates generally to systems and methods for detecting an optical change indicating the presence of an analyte and, more specifically, to systems and methods that can suppress a background physical interference during detection of the optical change.

In one aspect, the present disclosure can include a system including an optode sensor and an optical arrangement. The optode sensor can undergo the optical change in the presence of the analyte. The optical arrangement can provide illumination and detection of the optical change. The optode sensor can include a component configured to suppress the background physical interference during the detection.

In another aspect, the present disclosure can include an analyte sensor device. The analyte sensor device can include an optode layer that undergoes the optical change in the presence of the analyte. The optode layer can be encapsulated by a selectively-permeable membrane that that minimizes fouling of the analyte sensor device. The analyte sensor device can also include a plurality of microparticles that suppress the background physical interference on the detection of the optical change of the optode layer.

In a further aspect, the present disclosure can include a method for detecting the analyte in a sample. The optode can be exposed to the sample. An illumination source can provide the stable illumination of the optode. A detection device can detect the optical change in the optode that is indicative of the presence of the analyte in the sample. The optode can include the component configured to suppress the background physical interference from the sample during the detecting.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 8 shows an example of the experimental setup used to conduct the experiments;

FIG. 9 shows examples illustrating the suppression of a color of a sample by white Teflon microbeads dispersed in the selectively-permeable membrane encapsulating the optode layer.

DETAILED DESCRIPTION

I. Definitions

Figure 1:
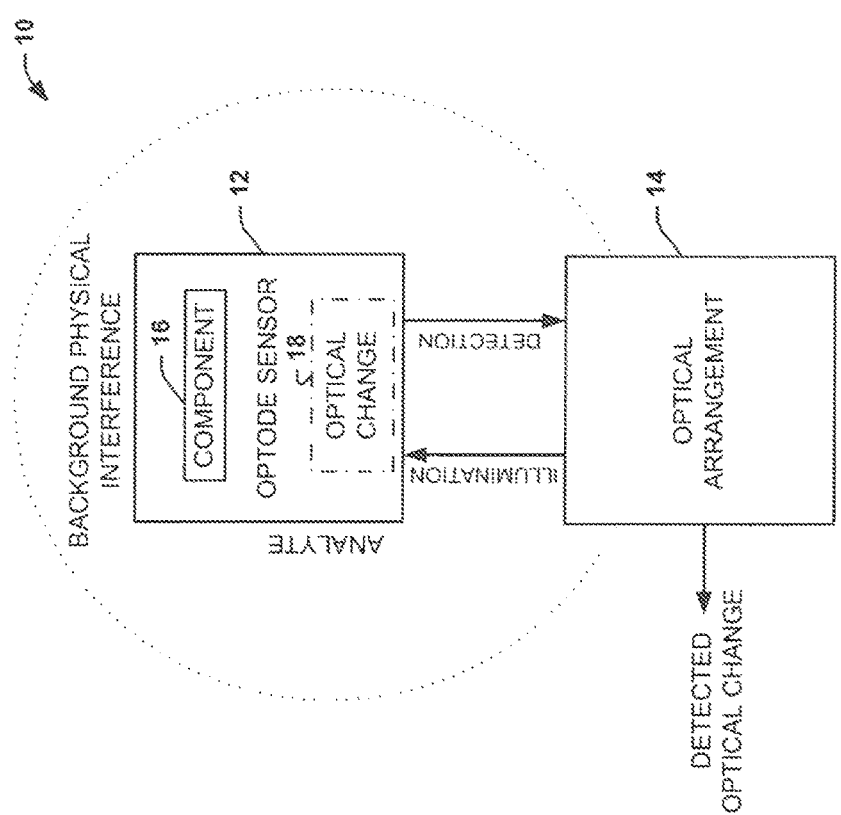
FIG. 1 shows a block diagram illustrating an example of a system that can detect an optical change indicating the presence of an analyte according to an aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure.

The sequence of operations (or acts/steps) is not limited to the order presented in the claims or figures unless specifically indicated otherwise.

As used herein, the term "optode", or "optrode", can refer to at least a portion of a sensor device that can undergo an optical change in the presence of an analyte. For example, the optical change can be a detectable change in an optical characteristic. In some instances, the optical change (e.g., a color change) can be qualitatively perceived or quantitatively detected.

As used herein, the term "analyte", can refer to a substance that is the subject of a chemical analysis. In some instances, the analyte can be present in a sample. In other instances, the analyte can be a reaction product (e.g., a reaction product of an enzymatic reaction).

As used herein, the term "sample", can refer to a specimen taken for scientific testing or analysis. Different examples of samples can include a biological/physiological product (e.g., blood, urine, tissue, etc.), water, soil, an agricultural product, and the like.

As used herein, the term "physical interference", can refer to a background hindrance or obstruction to the qualitative perception or quantitative detection of the optical change that is not due to a chemical reaction. The physical interference, for example, can be an optical signal (e.g., due to a color of the sample, an intrinsic fluorescence of the sample, etc.), a turbidity of the sample, an instability of the light source, or the like. In some instances, the physical interference can be referred to as a "background physical interference", a "physical feature" or the like.

As used herein, the term "suppress" can refer to a substantial reduction of the physical interference before or during the qualitative perception or quantitative detection of the optical change.

As used herein, the term "substantial suppression" can refer to a complete (e.g., 100%) or partial (e.g., less than 100%, such as about 90%, about 80%, about 70%, about 60%, or less than about 50%) reduction of the non-chemical interference before the qualitative perception or quantitative detection of the optical change.

As used herein, the term "microparticles" can refer to discrete particles that can be dispersed within at least a portion of the sensor device to facilitate suppression of the background physical interference. In some instances, microparticles can have a maximal diameter less than or equal to 100 microns. In other instances, the microparticles can have a maximal diameter less than or equal to 10 microns. In still other instances, the microparticles can have a maximal diameter less than or equal to 1 micron. In further instances, the microparticles can include nanoparticles. Examples of materials that can be used for the microparticles include, but are not limited to, metal oxides (e.g., titanium dioxide), carbon black, polymer materials (e.g., Teflon), glass, and the like.

As used herein, the term "qualitative" can refer to a quality that can be perceived by the naked eye. For example, the results of a qualitative measurement can include a description and/or observation.

As used herein, the term "quantitative" can refer to a quantity that can be measured. For example, the results of a quantitative measurement can include numerical data.

As used herein, the term "monochromatic" can generally refer to light of a single wavelength or frequency and/or containing or using a single color. When used in the context of illumination or detection, monochromatic can refer to a component (e.g., a light source, a detector, a camera, a filter, or the like) that is monochromatic or narrow-bandwidth.

II. Overview

At least a portion of an optode sensor can undergo a reversible optical change in the presence of an analyte without requiring any external power/wires. Accordingly, optode sensors have become viable alternatives to typical electrodes and other detection means for many different applications (e.g., analysis of a biological/physiological product, water, soil, an agricultural product, etc.). Accordingly, the present disclosure relates generally to systems and methods for detecting the optical change indicating the presence of the analyte. However, in many cases, the detection can be marred by a physical interference (e.g., an interference that is not chemical in nature). Accordingly, the present disclosure relates, more specifically, to systems and methods that can suppress the background physical interference during the detection of the optical change. For example, the background interference can be suppressed by a component of the optode sensor. For example, the component of the optode sensor can include a plurality of microparticles (e.g., made of Teflon, carbon black, metal oxide ($TiO_2$), or the like) that can be dispersed within a portion of the optode sensor.

III. Systems

One aspect of the present disclosure, as shown in FIG. 1, includes a system 10 that can detect an optical change 18 indicating the presence of an analyte. In some instances, the system 10 can be used to detect an analyte in an in vitro. For example, the analyte can be a biochemical species within a physiological sample, water, a soil sample, an agricultural sample, etc.

The system 10 can include an optode sensor 12 that can include an optode. At least a portion of the optode sensor 12 (e.g., including the optode) can undergo the optical change 18 in the presence of the analyte. For example, the optical change 18 can be a detectable change in an optical characteristic (e.g., a change in color). In some instances, the optical change 18 can be reversible so that the optode sensor 12 can be reused. This is unlike current electrochemical technologies (e.g., test strips) that are only good for a single measurement. Additionally, unlike other electrochemical technologies (e.g., electrodes), the optode sensor 12 does not require wires for operation. Thus, optode sensor 12 can provide a viable alternative for detecting an analyte in many different applications.

The system 10 can also include an optical arrangement 14. The optical arrangement 14 can illuminate at least a portion of the optode sensor 12. The optode sensor 12 can operate in a reflectance mode, where at least a portion of the optode sensor 12 facilitates a diffuse reflectance of at least a portion of the illuminated light based on the optical change 18. The optical arrangement 14 can detect the diffuse reflectance quantitatively and/or qualitatively. The detected diffuse reflectance can be correlated to optical change 18 and/or the concentration of the analyte. In some instances, the optical arrangement 14 can correlate the reflection to the presence of the analyte. In other instances, the optical arrangement 14 can send data related to the reflection to another device, which can correlate the reflection to the presence of the analyte.

In some instances, the detection of the diffuse reflectance can be marred by a physical interference. The physical interference can be any type of interference that is not chemical in nature. For example, the physical interference can be due to an optical signal (e.g., due to a color of the sample, an intrinsic fluorescence of the sample, etc.), a turbidity of the sample, an instability of the illumination, or the like. The optode sensor 12 can include a component 16 that can be configured to suppress the background physical interference during detection of the optical change 18.

As shown in FIGS. 2-5, the component 16 can include a dispersion of a plurality of microparticles. In some instances, the plurality of microparticles can facilitate the diffuse reflectance of the optode sensor 12 by filtering out or suppressing the background interference. For example, the background interference can be a color of an underlying sample, such as a biological fluid sample (e.g., serum or blood). The microparticles suppress the color from reaching the detector, enabling a detection of the optical change alone.

At least a portion of the plurality of microparticles can be substantially non-transparent in color. In some instances, at least a portion of the plurality of microparticles can be opaque, such opaque white microparticles constructed from a Teflon material or a metal oxide material (e.g., $TiO_2$) and/or opaque black microparticles constructed from a carbon black material. It will be appreciated that all of the microparticles can be formed from the same material or, alternatively, at least one of the microparticles can be formed from a material different than the material used to form the other microparticles. The microparticles can have the same or different average diameters. In some instances, the maximum average diameter of the microparticles can be 100 µm. In other instances, the maximum average diameter of the microparticles can be 1 µm. In further instances, the maximum average diameter of the microparticles can be 0.01 µm. In still further instances, the maximum average diameter of the microparticles can be 0.001 µm.

Figure 2:
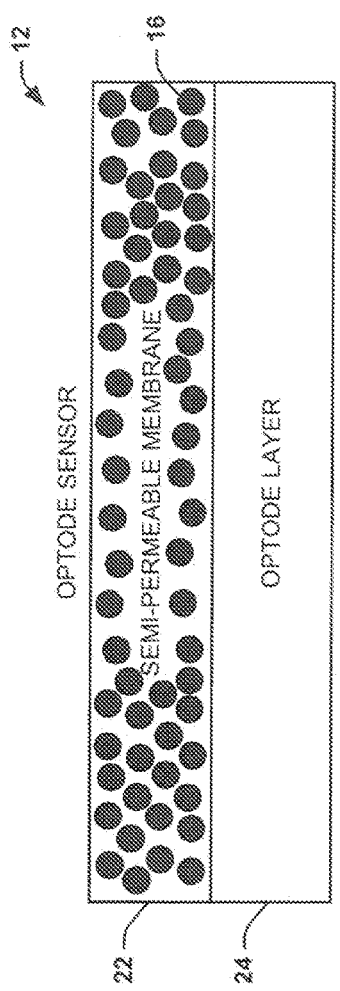
FIGS. 2-5 and 12 show blocks diagram illustrating example configurations of the optode sensor in FIG. 1.
Figure 3:
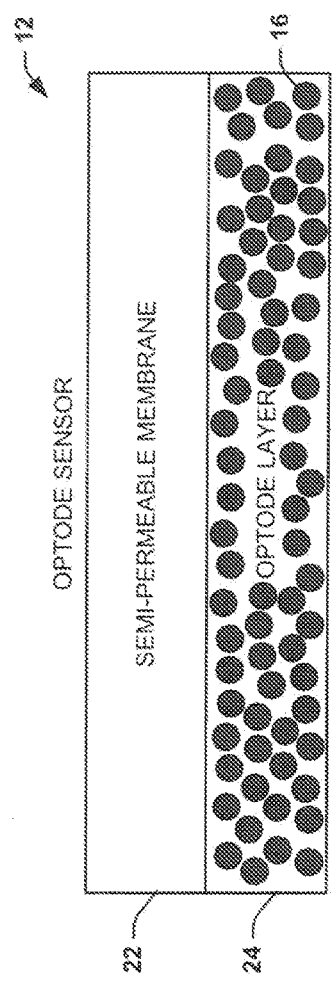
Figure 4:
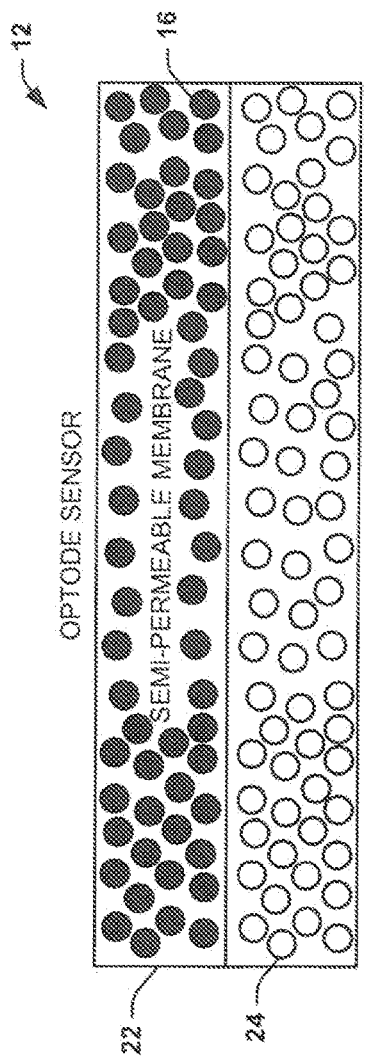
Figure 5:
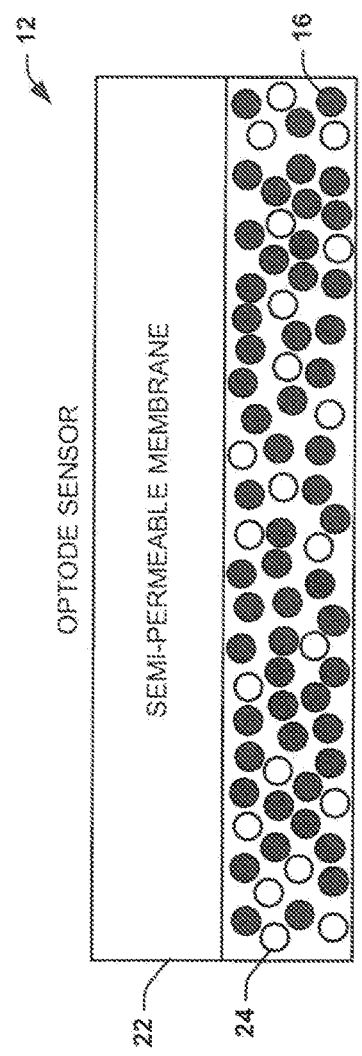
Figure 12:
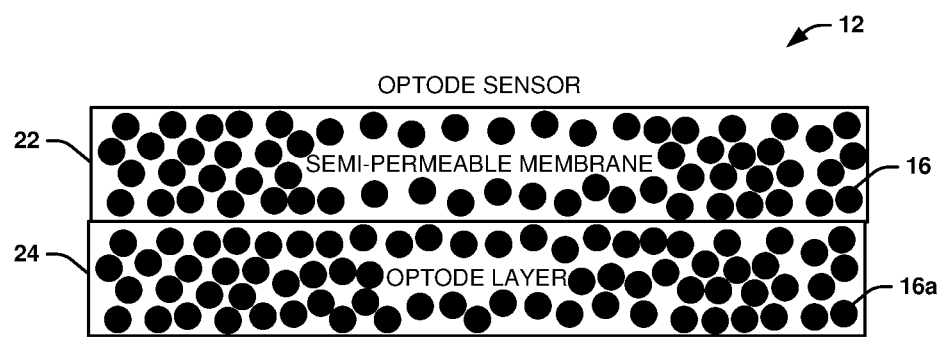

As shown in FIGS. 2-5, the optode sensor 12 can include a semi-permeable membrane 22 (or selectively-permeable membrane) and an optode layer 24. In some instances, as shown in FIGS. 3 and 5, the plurality of microparticles can be nanoparticles that are dispersed (randomly or uniformly) throughout the optode layer 24. In other instances, as shown in FIGS. 2 and 4, the plurality of microparticles can be dispersed (randomly or uniformly) and/or fixed within the semi-permeable membrane 22. Additionally, as shown in FIG. 12, the plurality of microparticles can be dispersed (randomly or uniformly) in both the optode layer 24 and the semi-permeable membrane 22.

The optode layer 24 can undergo the optical change in the presence of the analyte. The optical change does not depend on any binding equilibrium. Rather, the optical change can be based on a charge balance between ions that are taken up or released by at least a portion of the optode layer 24. In some instances, the optical change can be a color change indicative of the presence of the analyte. The optode layer 24 can be in the form of an optode membrane, as shown in FIGS. 2-3, or a plurality of optode beads, as shown in FIGS. 4-5.

In some instances, the optode layer 24 can include one or more indicator materials that undergo a chemical or physical change in response to the analyte or to a reaction product of the analyte. The indicator material may be a pH sensitive material (e.g., a dye) that is responsive to a pH change induced by an analyte or, more commonly, a detectable product by producing a color change (i.e., a change in the absorption wavelength, which may include wavelengths outside the visible range, such as in the IR range), fluorescence, or the like. The color change is reversible, depending upon the concentration of the analyte(s). Exemplary indicator materials, such as dyes, can include Congo red, neutral red, phenol red, methyl red, lacmoid, tetrabromophenolphthalein, α-naphtholphenol, and the like. A dye may be dissolved in organic solvent, such as (NPOE (2-nitrophenyl octyl ether), BEHS (bis(2-ethylhexyl)sebacate), DBE (dibenzyl ether), DOP (dioctyl phthalate), or the like.

In one example, the indicator material can include a light-absorbing, pH-sensitive dye that undergoes a color change in response to an analyte or a reaction product of the analyte. For instance, the indicator material can include a dye that is sensitive to hydrogen ions (i.e., pH) and is reversible (i.e., returns to its previous color when the pH returns to its previous level). Examples of pH-sensitive dyes can generally include ionophores, lipophilic anions, and lipophilic hydrogen ion sensitive dyes (also referred to herein as a chromoionophores). It will be appreciated that where ions other than hydrogen are to be detected, other dyes may be used. In such an arrangement, the ionophore can extract the ion to be detected and the lipophilic hydrogen sensitive dye can exhibit a corresponding color change.

Examples of chromoionophores can include one or more of:
chromoionophore I (9-(diethylamino)-5-(octadecanoylimino)-5H-benzo[a]phenoxazine), designated ETH5249;
chromoionophore II (9-dimethylamino-5-[4-(16-butyl-2, 14-dioxo-3,15 ioxaeicosyl)phenylimino] benzo[a] phenoxazine), designated ETH2439;
chromionophore III (9-(diethylamino)-5-[(2-octyldecyl) imino]benzo[a]phenoxazine), designated ETH 5350;
chromoionophore IV (5-octadecanoyloxy-2-(4-nitrophenylazo)phenol), designated ETH2412;
chromoionophore V (9-(diethylamino)-5-(2-naphthoylimino)-5H-benzo[a]phenoxazine);
chromoionophore VI (4',5'-dibromofluorescein octadecyl ester), designated ETH7075;
chromoionophore XI (fluorescein octadecyl ester), designated ETH7061; and combinations thereof (note that ETF is the designation of the Swiss Federal Institute of Technology).

Examples of lipophilic anions can include KTpClPB (potassium tetrakis(4-chlorophenyl)borate), NaHFPB (sodium tetrakis[3,5-bis(1,1,3,3,3-hexafluoro-2-methoxy-2-propyl)phenyl]borate), sodium tetrakis[3,5-bis(trifluoromethyl)phenyl]borate, sodium tetrakis(4-fluorophenyl)borate, combinations thereof, and the like.

Examples of ionophores can include sodium ionophores, potassium ionophores, calcium ionophores, and the like. Examples of sodium ionophores can include:
bis[(12-crown-4)methyl]2-dodecyl-2-methylmalonate, designated ETH227;
N,N',N''-triheptyl-N,N',N''-trimethyl4,4',4''-propylidynetris(3-oxabutyramide), designated ETH157;
N,N'-dibenzyl-N,N'-diphenyl-1,2-phenylenedioxydiacetamide, designated ETH2120;
N,N,N',N'-tetracyclohexyl-1,2-phenylenedioxydiacetamide, designated ETH4120;
4-octadecanoyloxymethyl-N,N,N',N'-tetracyclohexyl-1, 2-phenylenedioxydiacetamide), designated DD-16-C-5;
2,3:11,12-didecalino-16-crown-5), bis(benzo-15-crown-5); and combinations thereof.
Examples of potassium ionophores can include:
bis[(benzo-15-crown-5)-4'-methyl]pimelate, designated BME 44;
2-dodecyl-2-methyl-1,3-propanedil bis[N-{5'-nitro (benzo-15-crown-5)-4'-yl]carbamate], designated ETH1001; and combinations thereof.
Examples of calcium ionophores can include:
(–)-(R,R)—N,N'-bis-[11-(ethoxycarbonyl)undecyl]-N, N'-4,5-tetramethyl-3,6-dioxaoctane-diamide), designated ETH129;
N,N,N',N'-tetracyclohexyl-3-oxapentaned iamide, designated ETH5234;
N,N-dicyclohexyl-N',N'-dioctadecyl-3-oxapentanediamide), designated K23E1;
10,19-bis[(octadecylcarbamoyl)methoxyacetyl]-1,4,7,13, 16-pentaoxa-10,19-diazacycloheneicosane); and combinations thereof.

In one example, the optode layer 24 can have the following composition: about 50 mmol of chromoionophore ETH5350 (L); about 360 mmol sodium ionophore Na IV (I); about 55 mmol NaHFPB; and about 0.65 polyvinylchloride:

bis(2-ethylhexyl)sebacate. In this case, the equilibrium of such an optode layer 24 can be represented by the following equation:

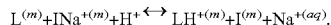

Additionally, the optode layer 24 can include one or more detection materials that can react with the analyte or catalyze a reaction of the analyte to produce a detectable reaction product. Or, the reaction/catalysis can result in an intermediate reaction product that undergoes further reaction/catalysis with a second or subsequent detection material to form a detectable product. For example, a first detection material can react with or catalyze the reaction of the analyte to produce an intermediate reaction product. A second detection material can then react with or catalyze the reaction of the intermediate reaction product to produce a detectable product. For example, the detection materials can include an enzyme catalyst. The enzymes glucose oxidase or glucose dehydrogenase may be used for the detection of glucose, the enzyme lactase may be used for detection of lactose, the enzyme galactose oxidase may be used for the detection of galactose, the enzyme urate oxidase may be used for the detection of uric acid, and the enzyme creatinine amidhydrogenase may be used for the detection of creatinine.

In an example, the optode layer 24 can be configured to detect the presence and/or concentration of glucose. The optode layer 24 can generally comprise, for example, a plasticized polymer, a chromoionophore, an ionophore, and a lipophilic anion. The optode layer 24 can further comprise an enzyme-loaded membrane, such as a glucose oxidase-loaded membrane. In the glucose oxidase-loaded membrane, the following enzyme reaction can occur:

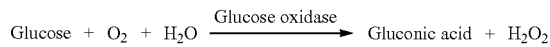

Because the above enzyme reaction produces gluconic acid, the pH in the optode layer 24 changes with changing concentration of glucose. The color (i.e., the absorption spectrum) of the pH indicator dye present in or on the enzyme-loaded membrane or the optode layer 24 will change due to the pH change in the membrane(s). It is this change in the spectrum that is detected and used to determine glucose concentration. Advantageously, such a glucose sensing system can detect glucose in the hypoglycemic range (e.g., below about 60 mg/dl).

The optode sensor 12 can also include a semi-permeable membrane 22 (or selectively-permeable membrane) that encapsulates the optode layer 24. In some instances, the semi-permeable membrane 22 can cover at least a top side of the optode layer 24. In other instances, the semi-permeable membrane 22 can cover at least 50% of the optode layer 24. In further instances, the semi-permeable membrane 22 can encapsulate the entire optode layer 24. The semi-permeable membrane 22 can be a substantially hydrophilic membrane that can provide both a protective and a functional role. The semi-permeable membrane 22 can be selective for specific molecules (e.g., the analyte or reaction product of the analyte), allowing the optical change and minimizing damage/fouling of the optode sensor 12.

Functionally, the semi-permeable membrane 22 can control the diffusion of target analyte and thereby lead to the improvement of linearity and dynamic range of the response of the optode sensor 12 (e.g., provide higher sensitivity and selectivity). For example, the semi-permeable membrane 22 can exclude anions, cations, lipids, and/or proteins. The composition of the semi-permeable membrane 22 can affect diffusion of charged ions. For example, phosphate ions from a biological fluid sample can diffuse through the semi-permeable membrane 22 and thereby increase the buffering capacity of the optode sensor 12. If the diffusion rate is slowed by selection of the materials used to form the semi-permeable membrane 22, the buffering capacity can be maintained at a low level and, thus, sensitivity can be increased. The composition of the semi-permeable membrane 22 can also affect the response time of the optode sensor 12. For example, high analyte permeability can allow for a very short response time.

In one example, the semi-permeable membrane 22 can comprise a negatively-charged hydrophilic gel, which includes at least one polyanion to reduce the buffering capacity of the optode sensor 12. Buffer capacity is the ability of the components of the optode sensor 12 to buffer the pH of a medium. When the buffer capacity is high, more acid is required to lower the pH than is the case when the buffer capacity is low. As a consequence, detection systems that are based on a change in pH become less sensitive. Where there is a large buffering capacity, the pH change is minimized and the system is less sensitive (e.g., it takes more acid to achieve a certain pH change). A semi-permeable membrane 22 comprising a negatively-charged hydrophilic gel thus allows the sensitivity of the optode sensor 12 to be adjusted.

The structure of the semi-permeable membrane 22 also permits control of the diffusion of analyte species, which allows the sensitivity of the optode sensor 12 to be controlled. For example, if low glucose concentrations are to be measured, the semi-permeable membrane 22 (and/or other aspects of the optode sensor 12) can be designed to be particularly sensitive. If high glucose concentration is to be measured, a lower sensitivity may be desired. The sensitivity of the semi-permeable membrane 22 to glucose concentration can be controlled, for example, by modifying the relative hydrophobicity of the semi-permeable membrane 22.

Depending on the protective and/or functional characteristics desired, the semi-permeable membrane 22 can be formed from any one or combination of polymeric, matrix-forming, and/or hydrogel materials. For example, the semi-permeable membrane 22 can include any one or combination of positively-charged cellulose, negatively-charged cellulose, BSA-glutaraldehyde, PEG, chitosan, cellulose acetate (CA) or cellulose acetate phthalate (CAP)-heparin, chitosan-heparin, polyurethane, polyvinyl pyrrolidone, acrylic polyester, fluorocarbons, silicone rubber, agar, HEMA, and the like. In one example, the semi-permeable membrane 22 can comprise a polyurethane film.

In some instances, the semi-permeable membrane 22 can have a multilayered structure (e.g., three layers: an outermost layer; a middle layer; and an inner layer). The outermost layer, which is exposed to a sample, can function as a protective layer and have a thickness of about 2-3 μm. The middle layer can function to regulate and limit the diffusion of an analyte (or analytes) to the optode layer 24 and be formed, for example, from polyurethane, polyvinylpyrrolidone, acrylic polyesters, vinyl resins, fluorocarbons, silicones, rubbers, HEMA, or combinations thereof. Polyurethane, for example, can be effective in slowing glucose diffusion relative to that of oxygen and downgrading glucose levels to below the Michaelis-Menten constant, rendering the overall response nearly linear. The middle layer can have a thickness of about 5-20 μm. The inner layer can include a negatively-charged layer to reduce the efflux of a reaction product (e.g., gluconic acid), which can lead to a further improvement in glucose sensitivity due to the reduction in gluconic acid efflux via the negatively-charge membrane. The inner layer may be formed from one or a mixture of polymer and/or matrix-forming materials, such as CA and CAP according to the desired sensitivity of the optode sensor 12.

Figure 6:
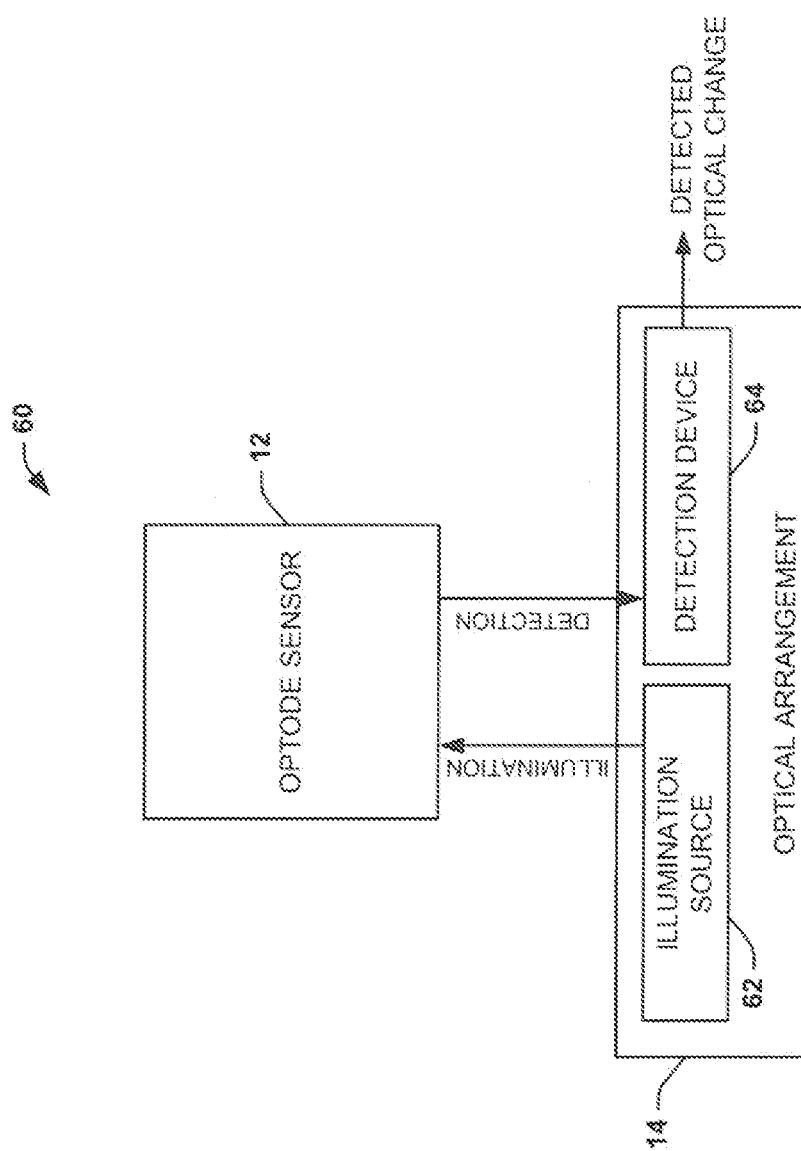
FIG. 6 shows a block diagram illustrating an example configuration of the optical arrangement in FIG. 1.

The plurality of microparticles can suppress background interference. The setup of the optical arrangement 14, as shown in FIG. 6, can further reduce the background interference (e.g., instability of the illumination source 62, significant overlap of the two absorption peaks whose ratio determines the color of the optode sensor 12) and/or increase portability of the system 60. The optical arrangement 14 can include an illumination source 62 that can provide a stable illumination of the optode sensor 12. For example, the illumination source 62 can include one or more LEDs (e.g., a set of narrow-band LEDs). In some instances, one or more filters can be coupled to the illumination source 62.

The optical arrangement 14 can also include a detection device 64 that can detect the diffuse reflectance of the optode sensor 12. In some instances, the detection device 64 can be a greyscale detector device. For example, the detection device 64 can be a CCD camera device or a grayscale camera. In some instances, the use of the illumination source 62 as one or more LEDs (e.g., a plurality of LEDs sequentially turned on) and the detection device 64 as a grayscale detector can increase the signal-to-noise ratio of the detection at least six-fold when compared to the detection with traditional white illumination and color camera detection schemes. In other instances, the detection device 64 can be a color image sensor. In still other instances, the detection device 64 can be a photodiode. In still other instances, the detection device 64 and the illumination source 62 can be accomplished with no imaging being used (e.g., through bifurcated or two-way optical fibers). In some instances, one or more filters can be coupled to the detection device 64.

IV. Methods

Figure 7:
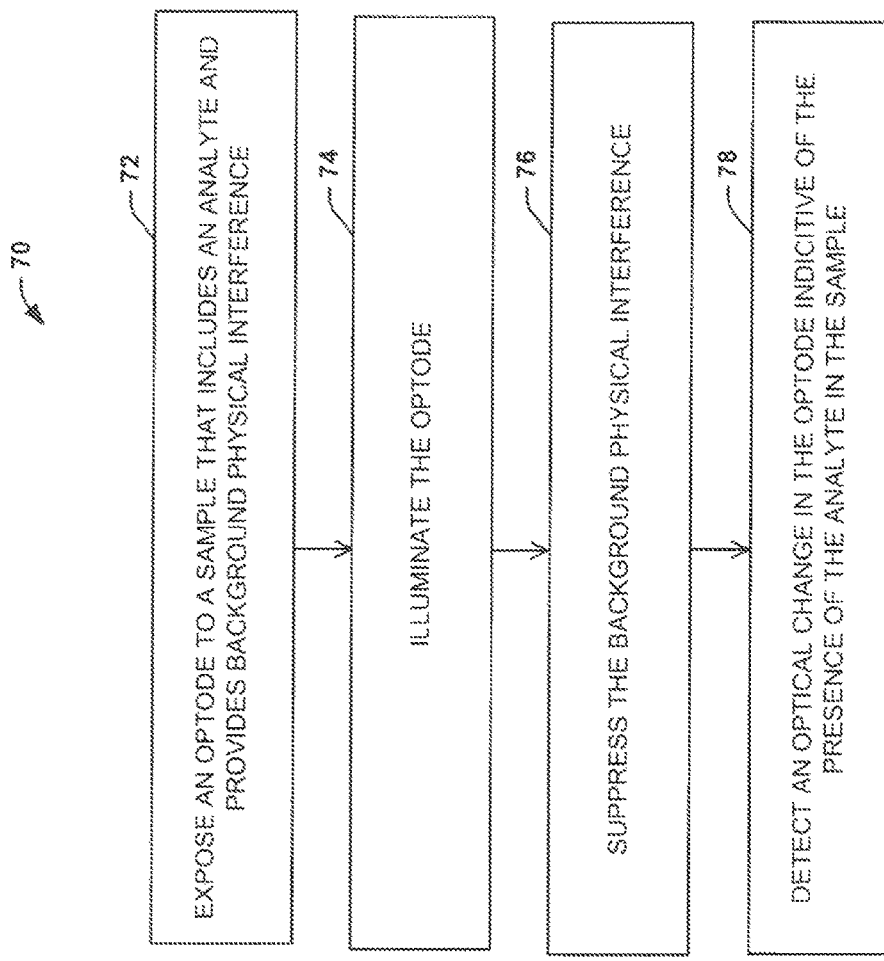
FIG. 7 shows a process flow diagram of a method for detecting an optical change indicating the presence of an analyte.

Another aspect of the present disclosure can include a method 70 for detecting an optical change indicating the presence of an analyte, as shown in FIG. 7. The method 70 is illustrated as a process flow diagram with flowchart illustrations. For purposes of simplicity, the method 70 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 70.

At 72, an optode (e.g., of optode sensor 12) can be exposed to a sample that includes an analyte and provides a background physical interference. In some instances, the background physical interference can be provided by an optical signal from the sample. For example, the sample can be blood or serum with a color that provides the background physical interference. In other examples, the sample can include water, soil, an agricultural product, or the like, that can provide the background physical interference.

In the presence of the analyte, the optode can undergo an optical change (e.g., a detectable change in an optical characteristic, like a color change). At 74, the optode can be illuminated (e.g., by optical arrangement 14). For example, the illumination can be provided by one or more LEDs (e.g., a set of one or more narrow band LEDs). At 76, the background physical interference can be suppressed (e.g., by component 16 of the optode sensor 12) from the diffuse reflectance of a light source of the illumination. To suppress the background physical interference, the optode can include a plurality of microparticles that are non-transparent and/or monochromatic. In some instances, the plurality of microparticles can be white (e.g., Teflon, a metal oxide like $TiO_2$, or the like). In other instances, the plurality of microparticles can be black (e.g., carbon black).

At 78, the optical change (e.g., optical change 18 in at least a portion of optode sensor 12) can be detected (e.g., by optical arrangement 14). The optical change can indicate the presence of the analyte in the sample. In some instances, the detection can be qualitative. In other instances, the detection can be quantitative. The quantitative detection can utilize a detection device, such as a grayscale CCD device.

V. Example

The following example is for the purpose of illustration only and is not intended to limit the scope of the appended claims.

Example 1

This example illustrates experiments using dispersions of white microparticles to suppress the color of the sample, which can interfere with the optical detection of the presence of an analyte in the sample. Results of these experiments are presented below.

Methods

Materials

Plasticizer bis(2-ethylhexyl) sebacate, DOS; pH chromoionophore III (ETH5350); sodium ionophore VI; potassium ionophore bis(benzo15-crown-5); ion-exchanger sodium tetrakis[3,5-bis(1,1,3,3,3-hexafluoro-2-methoxy-2-propyl)phenyl] borate; solvent tetra-hydro-furane, THF; poly(ethyleneglycol), PEG (Mr=600 g/mol), glucose oxidase, 2-(hydroxyethyl)methacrylate, HEMA, and poly(ethyleneglycol)methacrylate, PEGMA were bought from Sigma Aldrich (St. Louis, Mo.). Irgacure 651 UV photoinitiator was obtained from Ciba Specialty Chemicals (Florham Park, N.J.). Poly(methyl methacrylate), PMMA was from Plastics2000 (Modesto, Calif.). 5-μm Teflon microbeads were purchased from Schaff Plano Supply Company (Lake Zurich, Ill.). PVC beads and powder were obtained from Plastics. Cellulose acetate/cellulose acetate phthalate (CA/CAP beads) were made according to earlier protocols. Glass beads were made by diamond drilling into a glass slide.

Common chemicals including the dry salt mixture for making phosphate buffered saline, PBS, Titanium Dioxide ($TiO_2$), and 1 mm-thick glass cover slips were purchased from Sigma Aldrich.

Blood samples were obtained from University Hospitals (Cleveland, Ohio). Paramount Blood (Alcone, Long Island City, N.Y.) was also used for measurements of color interference studies with optodes with $TiO_2$ incorporated.

Apparatus

FIG. 8 shows the apparatus used for testing the efficacy of color exclusion of different bead preparations. Sensing wells (diameter 1 mm, depth 150 μm) were drilled in a glass substrate. Optode membranes (0.25 μl, 10 μm in thickness) were deposited in each sensing well and allowed to dry in air for 1 hour. A hydrogel layer made of PEG (MW 15000) was deposited above the optode membrane. The well was sealed with a protective UV polymerized membrane made of HEMA/PEGMA, another hydrogel that forms a stable membrane. The protective membrane prevented the optode membrane from biofouling by constituents of biomedical samples, including lipids. The sample (serum or blood in this work) was placed on top of the assembly.

White beads were dispersed in two ways: 1) Teflon powder within the hydrogel layer above the optode (FIG. 8A) and 2) TiO$_2$ nanoparticles dispersed within the optode membrane itself (FIG. 8B). The sensing device (FIG. 8C) includes a glass slide with several sensing wells and a white reference well above which a sample container is made from a PMMA sheet and attached using silicone elastomer.

The imaging setup is shown in FIG. 8D, where the camera and illumination sources were positioned underneath the sensor and reflectance images are recorded. Three types of optical setup were used for quantifying sensor response. The arrangement found to provide the best quality of results included a monochrome (greyscale) CCD chip with illumination provided by three each of red, green and blue LEDs (LST67F, LTT67C, and LBT67C—Osram Opto Semiconductors GmbH, Germany). The monochrome CCD chip was an IDS (UI-1225LE-M Imaging Development Systems, Obersulm, Germany) monochrome CCD chip with a USB 2.0 interface to a PC. The pixel resolution was 752×480, each pixel had 8 bits of monochrome intensity information. The micro video lens (NT57-684, Edmund Optics, Barrington, N.J.) had a 6.0 mm focal length and provided a field of view of approximately 15×8 mm at a minimum working distance of approximately 25 mm. All nine LEDs were mounted in a conical ring with their beam axis pointed to the center of the cone. The LEDs were spaced 40 degrees apart, with like colors 120 degrees apart. The LEDs were controlled by a circuit board, made in house, based on a PIC microcontroller (Microchip Technology, Chandler, Ariz., part number 12F675), which receives an input from a momentary pushbutton trigger, turns on the appropriate LED color for 10 ms and triggers the camera to take an image. Three images were taken automatically in succession, each with a different color LED providing illumination. White balance was achieved by adjusting the current in the three colors of LEDs such that images of a white background result in similar intensity values for red, green and blue illumination.

To compare the accuracy of the proposed monochrome CCD and color LED illumination system with commonly-used imaging setups, a laboratory grade, color camera was also tested (Scion CFW1012, Frederick, Md. USA) mounted on a microscope lens (VZM 1000 color system, Edmund Industrial Optics, Dunedin, Fla.) with a white illumination ring surrounding the objective. This imaging system is a scientific research quality system. A third system including a regular color camera, but with a manual setting in RAW image format that allows the complete disabling of any image post-processing (D5000, Nikon Corporation, Melville, N.Y.) with a ring-light source consisting of 48 white LEDs (NEEWER Ring 48, Edison, N.J.) was used to quantify response of sensing wells under colored samples.

Methods pH/Na$^+$ optodes were made according to standard procedures; briefly: from a mixture of PVC (60 mg), DOS (180 mg), the lipophilic pH-indicator chromoionophore III (0.5 mg), sodium ionophore (9.6 mg), and the ion exchanger (7.2 mg) dissolved in 1.5 mL THF to form a cocktail solution. Optode membranes were made by depositing 0.25 µl of the THF-based mixture onto the bottom of the sensor well. After evaporation of THF a membrane about 10 µm in thickness remained.

Two types of white bead dispersion were used. PEG was used as the hydrogel layer above the optode membrane, in which Teflon microbeads were dispersed (1:3 w/w Teflon:PEG), as shown in FIG. 8A. The protective membrane was made from HEMA, whose hydrophobicity can be increased by adding PEGMA. A mixture of 90% HEMA and 10% PEGMA and 0.1 w % photoiniator were dissolved in equal amount of DI water, wicked in between two slides kept 7 µm apart with aluminum foil spacers, and polymerized under UV light for 15 min. A PMMA sheet was used to make the sample holder, attached to the assembly using waterproof silicone. The second type of bead dispersion, shown in FIG. 8B, consisted of 60 mg TiO$_2$ nanoparticles dispersed within the cocktail solution. Serum and blood samples were diluted 6-fold with added PBS, adjusted to the desired pH with 0.1 M HCl or KOH. Red colored solutions were made using 1:5 (v/v) of paramount blood with the addition of PBS adjusted to specific pH values. To relate the color readings of the pH sensing wells to readings obtained with standard techniques a pH glass electrode (Fisher Scientific Waltham, Mass.) was used.

Data Analysis

ImageJ software was used to process the acquired images and extract the red, green and blue intensities for each pixel.

The color of a pixel in the acquired image is commonly represented as the relative intensities of red, green and blue components of the pixel (R, G, B). Using one of these values for measurement is insufficient as variations in illumination intensity will go undetected. Using one of the possible ratios eliminates this problem, however it does not compensate for eventual variations of the emission spectrum of the light source. A better way is to use all three color components for analysis and reference this to the color of a white reference as it appears to the detector, despite that only two colored forms of the chromoinophore are present in the membrane. This is because (a) the red and blue filters of the detector do not exactly coincide with the respective absorption maxima, and (b) measurement errors can be better compensated for by using a redundant scheme.

A particular apparent color can be represented as a vector in the 3D RGB space, and normalizing this vector to unit absolute value transforms a color to a point on the positive eighth of the unit sphere:

$$nX = \frac{X}{\sqrt{(R^2 + G^2 + B^2)}} \quad \text{(Equation 1)}$$

where X stands for detected R, G, or B which we call Pythagorean color normalization. The normalized color components of the white reference, nX$_w$ can be defined the same way. Normalized color components as well as ratios of white-referenced colors were used to represent results:

$$\left(\frac{R}{B}\right)_W = \frac{\left(\frac{nR}{nR_W}\right)}{\left(\frac{nB}{nB_W}\right)} = \left(\frac{R \cdot B_W}{B \cdot R_W}\right) \quad \text{(Equation 2)}$$

where subscript W means "white-referenced" values.

In comparing performance of each camera, the distance from the end of each individual, normalized vector to the end of the mean vector was calculated according to equation 3, where R$_m$ is the mean value of the red component, G$_m$ is the mean value of the green component and B$_m$ is the mean value of the blue component.

$$d = \sqrt{(R_i - R_m)^2 + (G_i - G_m)^2 + (B_i - B_m)^2} \quad \text{(Equation 3)}$$

The angle separating the i$^{th}$ vector from the mean vector is calculated from equation 4. Signal-to-noise ratio (SNR) was calculated for both the monochrome and color systems, according to equation 5.

$$\theta = 2 \cdot \arcsin\left(\frac{d}{2}\right) \quad \text{(Equation 4)}$$

$$SNR = \frac{\text{dynamic range (radians)}}{\text{standard deviation (radians)}} \quad \text{(Equation 5)}$$

Results
Comparison of the LED-Monochrome and White Light Source-Color Imaging Systems The raw, unprocessed RGB intensities were used for analysis of reflectance images obtained with color CCD, and raw greyscale intensities obtained with the greyscale CCD. This is because analyzing unprocessed primary information allows for objective comparison of the physical imaging setups, not skewed by any software processing.

In the RGB space after Pythagorean normalization (as described in Methods), a difference in color is represented by the angle between the two normalized unit color vectors that need to be compared.

Mean RGB vectors measured at low and high pH values are shown in Table 1. The computed S/N ratio (SNR) for each system is also shown in Table 1. These data indicate that the LED monochrome system provides broader dynamic range and much better SNR compared to the white illumination and color camera based imaging approach using the scientific Scion system. This finding can be rationalized by considering (1) the better stability of LEDs relative to typical white light sources, and (2) the narrow bandwidth of LEDs that make an overlap between the absorption peaks of the unbound (orange) and bound (blue) chromoionophore negligible at the bandpass wavelengths of the respective LEDs. The green LED is close to the isobestic point of the particular dye used and thus it may be used for intensity referencing.

TABLE 1

| System | pH Range | Angle between RGB Vectors (rad) | SNR |
|---|---|---|---|
| Color n = 9 | 6.0-9.4 | 0.797 | 250 |
| Monochrome n = 9 | 6.0-9.4 | 0.893 | 1490 |

Color Screening by White Microbeads Dispersed in Hydrogel

Several types of beads were dispersed in hydrogel above the optode membrane as shown in FIG. 8A. CA/CAP beads and glass beads gave good color insulation but glass beads could be dispersed more uniformly. Color exclusion was tested using glass beads in calibration experiments. Despite the good optical screening the dynamic range of response decreased relative to using just a white background. It was hypothesized that this is because the very large glass surface-to-volume ratio may act as a local pH buffer, due to the ability of glass to bind protons.

Therefore, Teflon microbeads were investigated and were found to provide good color screening and simultaneously were inert enough to not influence local pH. Over time (days) the color of the optode membrane became gradually fainter, likely due to some of the chromoionophore molecules partitioning onto the surface of lipophilic Teflon.

FIG. 9 illustrates the screening effect of Teflon dispersion in hydrogel above the optode membrane. The deep red background color in panel A of FIG. 9 is completely removed. Panel B of FIG. 9 shows pH calibration without and with Teflon dispersed in the hydrogel layer indicating little interference with pH response. Panel C of FIG. 9 shows the screening effect of Teflon beads under a drop of blood. The red color of blood together with the blue of the membrane at pH 6.0 results in a very dark back reflected image when there is no screening (panel A of FIG. 9, left). The grey-orange color of the membrane at pH 7.5 barely changes the hue of the dark image of the sensor (Panel B of FIG. 9, left). Adding Teflon beads to the hydrogel filters out the red of the blood sample to an extent that the expected blue of the membrane at pH 6.0 became clearly visible (Panel A of FIG. 9, right). The color change from pH 6 to 7.5 was significant and similar to what is seen in calibration in clear buffer.

Suppression of Sample Color by White Nanoparticles in the Optode Membrane

Figure 10:
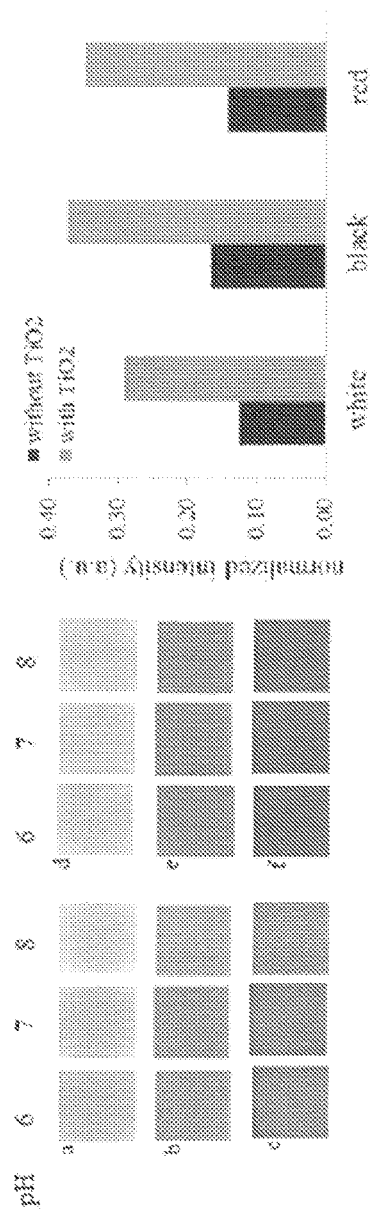
FIGS. 10 and 11 show examples illustrating the suppression of a color of a sample by white $TiO_2$ nanoparticles dispersed within the optode layer.
Figure 11:
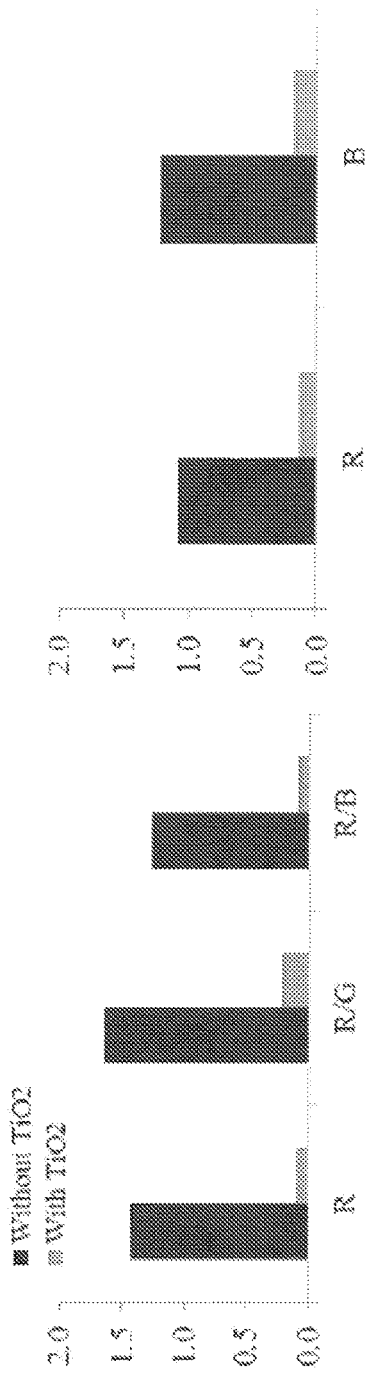

A dispersion of $TiO_2$ nanoparticles within the optode membrane itself was also tested, as shown schematically in FIG. 8B. $TiO_2$ is inert and can be loaded into the membrane at a high density without decreasing the dynamic range of response or increasing response time. Results are shown in FIG. 10. Despite a visible influence of background color even in the presence of $TiO_2$ nanoparticles in the membrane, the suppression of color interference is very significant as shown in FIG. 11. The effect of the nanoparticles on R/B is shown in FIG. 11 for each of the background colors (relative to white). The greatest effects were seen with red background, followed by blue background. The effect of screening is less with green background. The use of red/blue ratio explains why both red and blue backgrounds have a much greater effect than green.

Data obtained with white and red backgrounds are analyzed in FIG. 11 in terms of both mean values, described by equation 6, where $R_w$ and $R_r$ represent the normalized red intensity with white or red backgrounds, respectively, n is total number of measurements taken, and $R_{dynamic\ range}$ represents the dynamic range between red intensity at high and low pH values. In FIG. 11, the left panel shows a paper background and right panel shows with PBS-diluted Paramount blood solution.

$$\frac{\sum_{n=6} R_w - R_r}{n} \Big/ R_{dynamic\ range} \quad \text{(Equation 6)}$$

The effect of changing from white to red background is very little when $TiO_2$ is present as compared to the large effect without $TiO_2$. This is seen in R, but similar improvement is seen in ratios also (R/G, R/B).

Besides reducing color interference from the sample, the dynamic range in colors also increased with $TiO_2$ present, as shown in FIG. 10, right panel. This is because the membrane's proper color is reflected back to the camera more efficiently than without the beads. The dispersion also created much longer backscattering paths than the thickness of the membrane, which contributed to creating brighter colors. This is not seen with a white background alone because the optical path length across the membrane is just double the thickness without the nanoparticles. There is a limit, however, to the size of TiO$_2$ nanoparticles that provide both elimination of background color interference and improvement of dynamic range. When 20 nm sized particles were used, while the screening effects of the optode remain, the dynamic range reduces to equivalent of an optode without TiO$_2$, likely due to a decrease in light scattering of nanoparticles.

From the above description, those skilled in the art will perceive improvements, changes and modifications. Such improvements, changes and modifications are within the skill of one in the art and are intended to be covered by the appended claims.

What is claimed is:

1. A system comprising:
    an optode sensor comprising:
        an optode layer that undergoes an optical change in the presence of an analyte, wherein the optode layer comprises an optode membrane and a plurality of optode beads and one or more indicator dyes that undergo the optical change in the presence of the analyte; and
        a selectively-permeable membrane encapsulating the optode layer that minimizes fouling of the optode sensor; and
    an optical arrangement that provides illumination of a sample comprising the analyte and detection of the optical change of the optode layer in the presence of the analyte,
    wherein a plurality of non-transparent nanoparticles are dispersed throughout the optode layer to suppress background physical interference on the detection of the optical change.

2. The system of claim 1, wherein the background physical interference comprises an optical signal from the sample that includes the analyte.

3. The system of claim 1, further comprising another plurality of microparticles dispersed within the selectively-permeable membrane.

4. The system of claim 1, wherein the optical arrangement comprises at least one light emitting diode to provide the illumination and a detection device to perform the detection.

5. The system of claim 4, wherein the optical arrangement further comprises at least one filter coupled to at least one light emitting diode or the detection device.

6. An analyte sensor device comprising:
    an optode layer that undergoes an optical change in the presence of an analyte, wherein the optode layer comprises an optode membrane and a plurality of optode beads and one or more indicator dyes that undergo the optical change in the presence of the analyte; and
    a selectively-permeable membrane encapsulating the optode layer that minimizes fouling of the analyte sensor device; and
    a plurality of non-transparent nanoparticles dispersed throughout the optode layer that suppress a background physical interference on a detection of the optical change of the optode layer.

7. The analyte sensor device of claim 6, wherein the physical interference comprises an optical signal from a sample that includes that analyte.

8. The analyte sensor device of claim 6, wherein the optode layer comprises the optode membrane, and wherein the plurality of nanoparticles are dispersed within the optode membrane.

9. The analyte sensor device of claim 6, wherein another plurality of nanoparticles are dispersed within the selectively-permeable membrane.

10. The analyte sensor device of claim 6, wherein the plurality of nanoparticles comprise at least one of a material comprising TiO$_2$ and a carbon black material.

11. A method for detecting an analyte in a sample, the method comprising the steps of:
    exposing an optode sensor to the sample, wherein the optode sensor comprises:
        an optode layer that undergoes an optical change in the presence of an analyte, wherein the optode layer comprises an optode membrane and a plurality of optode beads and one or more indicator dyes that undergo the optical change in the presence of the analyte; and
        a selectively-permeable membrane encapsulating the optode layer that minimizes fouling of the optode sensor,
        wherein a plurality of non-transparent nanoparticles that suppress a background interference on the detection of the optical change are dispersed throughout the optode layer;
    providing, by an illumination source, an illumination of a sample comprising the analyte; and
    detecting, by a detection device, an optical change in the optode sensor indicative of the presence of the analyte in the sample in response to the illumination.

12. The method of claim 11, wherein the background interference is provided by an optical signal from the sample.

13. The method of claim 11, wherein the illumination source comprises at least one light emitting diode.

* * * * *